United States Patent [19]
Müller et al.

[11] Patent Number: 5,455,236
[45] Date of Patent: Oct. 3, 1995

[54] 5,10-METHYLENETETRAHYDROFOLIC ACID-CYCLODEXTRIN INCLUSION COMPOUNDS

[75] Inventors: Hans R. Müller, Schaffhausen; Martin Ulmann, Dachsen; Josef Conti, Schaffhausen, all of Switzerland

[73] Assignee: Eprova Aktiengesellschaft, Schaffhausen, Switzerland

[21] Appl. No.: 90,688

[22] Filed: Jul. 12, 1993

[30] Foreign Application Priority Data

Jul. 13, 1992 [CH] Switzerland .................. 2192/92

[51] Int. Cl.$^6$ .......... A61K 31/715; A61K 31/505; C08B 37/16; C07D 475/00
[52] U.S. Cl. ............... 514/58; 514/260; 514/259; 514/274; 544/258; 544/287; 536/103
[58] Field of Search ............... 514/260, 259, 514/58; 544/258, 287; 536/103

[56] References Cited

U.S. PATENT DOCUMENTS

| | | | |
|---|---|---|---|
| 4,350,659 | 9/1982 | Riceberg | 422/61 |
| 4,447,608 | 5/1984 | Jones et al. | 544/287 |
| 4,564,616 | 1/1986 | Jones et al. | 514/260 |
| 4,857,530 | 8/1989 | Berman et al. | 514/259 |
| 4,959,472 | 9/1990 | Wood et al. | 544/258 |
| 5,194,611 | 3/1993 | Marazza et al. | 544/258 |

FOREIGN PATENT DOCUMENTS

| | | |
|---|---|---|
| 0409125 | 7/1990 | European Pat. Off. . |
| 0427078 | 10/1990 | European Pat. Off. . |
| 0495204 | 12/1991 | European Pat. Off. . |
| 59-175432 | 10/1984 | Japan . |
| 62-281855 | 12/1987 | Japan . |
| 9117660 | 5/1991 | WIPO . |
| 91/17660 | 11/1991 | WIPO . |

OTHER PUBLICATIONS

Armstrong et al., "Separation of Drug Stereoisomers by the Formation of β-Cyclodextrin Inclusion Complexes", Science, 232:1132–1135 (May 30, 1986).

Primary Examiner—Douglas W. Robinson
Assistant Examiner—Howard C. Lee
Attorney, Agent, or Firm—Millen, White, Zelano & Branigan

[57] ABSTRACT

The invention relates to novel cyclodextrin inclusion compounds of 5,10-methylenetetrahydrofolic acid. The surprisingly good stability of these compounds makes possible their pharmaceutical use for the first time. The invention additionally relates to a process for the preparation of the said substances and their use for the preparation of medicaments.

16 Claims, No Drawings

5,10-METHYLENETETRAHYDROFOLIC ACID-CYCLODEXTRIN INCLUSION COMPOUNDS

SUMMARY OF THE INVENTION

The invention relates to α-, β-, γ-, hydroxypropyl-β-, hydroxypropyl-γ-, dimethyl-β- and dimethyl-γ-cyclodextrin inclusion compounds of (6R)-, (6S)- and (6R,S)-5,10-methylenetetrahydrofolic acid. The surprisingly good stability of these compounds makes possible for the first time their pharmaceutical use.

The invention additionally relates to a process for the preparation of the said substances and also their use for the preparation of medicaments.

In the following, hydroxypropylcyclodextrin is in each case to be understood as meaning hydroxypropylcyclodextrin (0.6), hydroxypropylcyclodextrin (0.9), 3-hydroxypropylcyclodextrin, 2,3-dihydroxypropylcyclodextrin and in particular 2-hydroxypropylcyclodextrin. Also in the following, 5,10-methylenetetrahydrofolic acid is also to be understood as meaning 5,10-methylenetetrahydrofolic acid salts, in particular alkali metal and alkaline earth metal salts.

Tetrahydrofolates are the biologically active forms of folic acid (folic acid cofactors). As medicaments, tetrahydrofolates are mainly used as the calcium salt of 5-formyl-5,6,7,8-tetrahydrofolic acid [leucovorin], e.g., for enhancing the therapeutic effect of 5-fluorouracil or, e.g., as a rescue substance when using methotrexate in cancer therapy. In the body, (6S)-5-formyltetrahydrofolic acid is converted to (6R)-5,10-methylenetetrahydrofolic acid, which, as a cofactor, forms a cytostatic covalent ternary complex, 5-F-dUMP/TS/5,10-methylenetetrahydrofolic acid, from 5-fluorodeoxyuridine monophosphate (5-F-dUMP) formed from 5-fluorouracil (5-FU), and thymidylate synthetase (TS). For this see W. A. Bleyer, Cancer, March 15 Supplement 1989: pp. 995–1007 and E. L. R. Stokstad, Folic Acid Metabolism in Health and Disease 1990 (Wiley-Liss Inc), page 9.

It would therefore be advantageous to use the cofactor 5,10-methylenetetrahydrofolic acid directly instead of leucovorin (5-formyltetrahydrofolic acid). For this see WO 91/17660 page 5, lines 24 to 35. Until now, this undertaking failed because of the inadequate purity and stability of 5,10-methylenetetrahydrofolic acid and its salts. For this compare EP 0,409,125; the purities of (6R,S)-5,10-methylenetetrahydrofolic acid described therein are in general between 85 and 90%. Only from the calcium and magnesium salt of (6R,S)-5,10-methylenetetrahydrofolic acid were preparations having a purity of 96.5–98.8% obtained. The stability of the salt solutions, however, is very critical. At pH 9 only about 85% of the original amount of 5,10-methylenetetrahydrofolic acid is still present after 6 hours. For this see EP 0,409,125, table, page 14.

5,10-Methylenetetrahydrofolic acid in solution is in equilibrium with formaldehyde and tetrahydrofolic acid. For this see L. J. Machlin, Handbook of Vitamins, 2nd Ed. (Marcel Decker Inc., New York/Basle), T. Brody page 457; M. J. Osborn et al., J. Am. Chem. Soc. 82, 4921 (1960), R. G. Kallen et al., J. Biol. Chem., 241, 5851 (1966), Moran et al., Proc. Natl. Acad. Sci. USA 76, 1456–1460 (1979). This equilibrium stands in the way of the parenteral use of 5,10-methylenetetrahydrofolic acid. Also in WO 91/17660, which intensively examines the advantages of the use of 5,10-methylenetetrahydrofolic acid compared with other tetrahydrofolic acid derivatives, no possibility for the stabilization of 5,10-methylenetetrahydrofolic acid is demonstrated. However, this stabilization is the basis which makes possible a pharmaceutical use of 5,10-methylenetetrahydrofolic acid in the first place. Previously known technologies, such as the addition of ascorbic acid, parabens, mercaptoalcohols or trometamol used for the stabilization of 5-formyltetrahydrofolic acid, for this see EP 0,416,232, or the stabilization of the calcium salt of 5-formyltetrahydrofolic acid by addition of a complexing agent for the alkaline earth metal ion, for this see EP 0,401,895, cannot be used for 5,10-methylenetetrahydrofolic acid or only have limited success, e.g. by slowing down the oxidative degradation of tetrahydrofolic acid and tetrahydrofolic acid derivatives. None of these methods, however, affects the equilibrium of 5,10-methylenetetrahydrofolic acid with tetrahydrofolic acid and free formaldehyde.

It is clear that the use of β-cyclodextrin for the stabilization of dihydrofolic acid, which can be used as a substrate in the biochemical analysis of methotrexate (JP 58-48933 Sho) and the use of cyclodextrin for the stabilization of leucovorin (EP 0,427,078) are also clearly directed at the inhibition of oxidative degradation.

It has now surprisingly been found that tetrahydrofolic acid also undergoes the condensation reaction with formaldehyde in the presence of cyclodextrins and in particular that stable inclusion compounds of 5,10-methylenetetrahydrofolic acid in the corresponding cyclodextrin result after reaction in aqueous solution and, as a result, the therapeutic use of 5,10-methylenetetrahydrofolic acid in aqueous solutions is made possible for the first time.

The increase in stability is all the more surprising, as previous measurements allowed the conclusion that virtually no interaction between tetrahydrofolates and cyclodextrin took place. For this see D. W. Armstrong, et al., Science, 232, 1132–5, (1986), specifically page 134, column 2, line 2. It was possible to confirm by in-house measurements that cyclodextrin does not interact with 5-formyltetrahydrofolic acid and only extremely weakly with 5-methyltetrahydrofolic acid. A stabilization of 5,10-methylenetetrahydrofolic acid with respect to chemical degradation, but in particular also with respect to a shift in the equilibrium of free formaldehyde and tetrahydrofolic acid to 5,10-methylenetetrahydrofolic acid could therefore not be expected.

The cyclodextrin inclusion compounds are preferably prepared by reaction, with formaldehyde in the presence of the corresponding cyclodextrin, from (6S)-, (6R)- and (6R, S)-tetrahydrofolic acid sulfate or sulfonic acid salt, which have become easily accessible due to European Patent Application EP-0,495,204, in situ or after prior isolation or liberation and purification. For quantitative reaction of the tetrahydrofolic acid only small molar excesses of formaldehyde of at most about 10–20% are necessary here. The reaction is preferably carried out in the pH range of about 8–9. However, the inclusion compound can also be obtained by introducing (6R)-, (6S)- or (6R,S)-5,10-methylenetetrahydrofolic acid into a cyclodextrin solution or cyclodextrin suspension or by triturating (6R)-, (6S)- or (6R,S)-5,10-methylenetetrahydrofolic acid and cyclodextrin in solid form. The products obtained are stable in solution at room temperature. They are suitable as constituents of parenteral pharmaceutical forms or as a starting material for the production of oral pharmaceutical forms. Both the oral and the parenteral pharmaceutical forms are suitable, e.g., for cancer therapy, for the treatment of certain forms of anaemia, of autoimmune diseases and of neural disorders.

The (6R)-, (6S)- or (6R,S)-5,10-methylenetetrahydrofolic acid-cyclodextrin inclusion compounds are preferably administered at a dosage of about 30–5000 mg/m² body surface area, especially 100–2000 mg/m². Parenteral forms can be, for example, dissolved in normal saline (0.89% w/v) optionally containing dextrose and also optionally containing antioxidant stabilizers such as ascorbic acid or reduced glutathione. Preferably, solutions are made with sterile, deaerated water having a concentration of about 0.1–500 mg/ml. The pH of the solution to be injected can range from slightly acidic to slightly alkaline.

5,10-methylenetetrahydrofolic acid-cyclodextrin inclusion compounds can be administrated as a bolus or as a continuous infusion before, concurrently or after the application of an anti-cancer drug such as 5-fluorouracil. For example, besides concurrent use, the 5,10-methylenetetrahydrofolic acid-inclusion complex can be administered preferably about 6–24 hours, especially 1–3 hours prior to administration of 5-fluorouracil. They can also be administered preferably about 1–10 days, especially 1–6 hours subsequent to administration of 5-fluorouracil.

The invention relates to novel inclusion compounds, for example, α-, β-, γ-, hydroxypropyl-β-, hydroxypropyl-γ-, dimethyl-β- and dimethyl-γ-cyclodextrin inclusion compounds of (6R)-, (6S)- and (6R,S)-5,10-methylenetetrahydrofolic acid. These products are stable in aqueous solution. They are also suitable for the production of parenteral pharmaceutical forms, e.g., in cancer therapy.

On account of the high solubility and physiologically good tolerability, alkali metal or alkaline earth metal salts, specifically the sodium potassium, calcium or magnesium salt of 5,10-methylenetetrahydrofolic acid, are particularly suitable for the preparation of these compounds. At a similar purity compared to the calcium salt, the magnesium salt of 5,10-methylenetetrahydrofolic acid has a solubility which is about ten times higher and the solubility of the sodium and the potassium salts is still higher. These substances are therefore especially to be emphasized in the preparation of pharmaceutical products.

Preferred compounds are:

alkali metal or alkaline earth metal salts of (6R)- and (6S)-5,10-methylenetetrahydrofolic acid with β-cyclodextrin alkali metal or alkaline earth metal salts of (6R)- and (6S)-5,10-methylenetetrahydrofolic acid with hydroxypropyl-β-cyclodextrin alkali metal or alkaline earth metal salts of (6R)- and (6S)-5,10-methylenetetrahydrofolic acid with hydroxypropyl-γ-cyclodextrin alkali metal or alkaline earth metal salts of (6R)- and (6S)-5,10-methylenetetrahydrofolic acid with γ-cyclodextrin alkali metal or alkaline earth metal salts of (6R)- and (6S)-5,10-methylenetetrahydrofolic acid with dimethyl-β-cyclodextrin where in each case the natural (6R)-form of 5,10-methylenetetrahydrofolic acid is to be preferred for the preparation of the inclusion compound.

The invention further relates to the process for the preparation of stable cyclodextrin inclusion compounds of 5,10-methylenetetrahydrofolic acid, which is characterized in that 5,10-methylenetetrahydrofolic acid or a derivative of 5,10-methylenetetrahydrofolic acid is reacted with α-, β- or γ-cyclodextrin or a derivative of α-, β- or γ-cyclodextrin and, if desired, the 5,10-methylenetetrahydrofolic acid-cyclodextrin inclusion compound obtained is isolated.

In addition, the invention relates to a process for preparation of stable cyclodextrin inclusion compounds of 5,10-methylenetetrahydrofolic acid, which is characterized in that tetrahydrofolic acid or a salt of tetrahydrofolic acid is preferably reacted with the corresponding cyclodextrin, if desired converted into another salt or the acid is liberated, and then the 5,10-methylene tetrahydrofolic acid-cyclodextrin inclusion compounds are prepared in situ by addition of formaldehyde and, if desired, the 5,10-methylenetetrahydrofolic acid-cyclodextrin inclusion compound obtained is isolated.

Preferred salt components of 5,10-methylenetetrahydrofolic acid or of tetrahydrofolic acid here are pharmaceutically tolerable cations such as sodium, potassium, magnesium or calcium, or anions such as sulfates, sulfonates or halides.

The cyclodextrins used in the inclusion compounds according to the invention are α-, β- or γ-cyclodextrin or a derivative of α-, β- or γ-cyclodextrin. Preferably, the cyclodextrin derivatives are alkylated or hydroxyalkylated α-, β- or γ-cyclodextrins containing 1-3 substituents per cyclodextrin molecule. The alkyl and hydroxyalkyl substituents preferably contain 1–3 C atoms and 0–2 hydroxy groups.

Preferred cyclodextrin inclusion compounds are formed with cyclodextrins such as β-, hydroxypropyl-β-, dimethyl-β-, γ-, hydroxypropyl-γ- or dimethyl-γ-cyclodextrin. The cyclodextrins are preferably employed in at least molar ratios of about 1:1 or about 2:1 to the 5,10-methylenetetrahydrofolic acid. The use of highly concentrated cyclodextrin solutions is advantageous here. Mixtures of various cyclodextrins can also be employed. Depending on the intended application, a specific salt of 5,10-methylenetetrahydrofolic acid, a specific cyclodextrin or a specific ratio of 5,10-methylenetetrahydrofolic acid to the cyclodextrin may be preferred. The optimum conditions can be determined by simple experiments.

The reaction of tetrahydrofolic acid with formaldehyde in the presence of cyclodextrin is preferably carried out in a solvent consisting of water or a water-miscible organic solvent such as lower aliphatic carboxylic acid or a lower alcohol.

Owing to the sensitivity to oxidation of tetrahydrofolic acid, the use of protection against oxidation is recommended.

The isolation of the cyclodextrin inclusion compound is carried out by means of known techniques such as, e.g., evaporation of the solvent at elevated temperature in vacuo, crystallization, lyophilization or precipitation by addition of an organic solvent. The cyclodextrin inclusion compound can also be prepared by trituration of 5,10-methylenetetrahydrofolic acid and cyclodextrin in solid form.

The invention also relates to the use of (6R)-, (6S)- or (6R,S)-5,10-methylenetetrahydrofolic acid or its salts as an inclusion compound in α-, β-, or γ-cyclodextrin or of its derivatives as a constituent or as a starting material for the preparation of medicaments.

The applications for (6R)-, (6S)- or (6R, S)-5,10-methylenetetrahydrofolic acid-cyclodextrin inclusion compounds are quite significant and far-reaching. For example, antitumor uses of these compounds, combined with thymidylatsynthetase inhibitory fluoropyrimidines include: (1) addition to Platinol/5-fluorouracil infusion therapy in head and neck cancer and other epidermoid cancers, (2) addition to combination cyclophosphamide/doxorubicin/5-fluorouracil in breast cancer, and (3) addition to topical Efudex® (5-fluorouracil) cream under an air-free occlusive dressing for skin conditions (for example, benign keratoses, keratoacanthomas, verrucae, premalignant keratoses, in situ cancer and invasive superficial malignancies amenable to topical therapy. Furthermore, (6R)-, (6S)- or (6R,S)-5,10-methylenetetrahydrofolicacid-cyclodextrin inclusion compounds can also be applied to those cancer types in which 5-fluorouracil and floxuridine are typically combined with leucovorin, such as in colon, rectal and pancreatic carcinomas.

(6R)-, (6S)- or (6R, S)-5,10-methylenetetrahydrofolic acid-cyclodextrin inclusion compounds can also be utilized with respect to non-malignancy related conditions. For example, these compounds can be used with respect to $B_{12}$- and $B_6$-refractory anemias which are not responsive to leucovorin. They can also be used to treat folate deficiencies. Furthermore, they can also be used for the potentiation (selective rescue of the host patient) of the thymidylatsynthetase inhibitory mechanism of antibacterial action of nucleotide analogs.

Additionally, (6R)-, (6S)- or (6R, S)-5,10-methylenetetrahydrofolic acid-cyclodextrin inclusion compounds can be utilized to reduce the toxicity of anti-folate drugs which have been administered to patients. Such antifolate drugs include, for example, methotrexate, trimetrexate, nitrous oxide and dideoxytetrahydrofolic acid.

As a rescue agent following methotrexate, (6R)-, (6S)- or (6R,S)-5,10-methylenetetrahydrofolic acid-cyclodextrin inclusion compounds are likely to be more specific than the presently used leucovorin since they would require less metabolic activation. They could also become useful in rescue of the host in the trimetrexate treatment of *Pneumocystis carinii* infections of immunosuppressed patients (i.e., AIDS patients).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding Swiss application 02192/92-0, filed Jul. 13, 1992, are hereby incorporated by reference.

EXAMPLES

Example 1

Stability of cyclodextrin inclusion compounds of 5,10-methylenetetrahydrofolic acid and its salts in solution a) Stability of sodium and calcium salt solutions of (6R)- and (6S)-5,10-methylenetetrahydrofolic acid at 23° C. in phosphate buffer

| | Weeks | | | | | |
|---|---|---|---|---|---|---|
| | 1 | 2 | 4 | 5 | 7 | 14 |
| Na salt of (6R)-CH$_2$-THF without cyclodextrin under nitrogen | 91.1 | 64.4 | 30.5 | 18.1 | 16.7 | — |
| Na salt of (6R)-CH$_2$-THF β-cyclodextrin | — | 92.3 | — | — | — | 88.5 |
| Na salt of (6S)-CH$_2$-THF β-cyclodextrin | 100.0 | 84.8 | — | 75.0 | — | — |
| Na salt of (6R)-CH$_2$-THF α- + β-cyclodextrin (1:1:1) | 100.0 | 95.8 | 94.3 | 83.2 | 78.5 | 73.0 |
| Ca salt of (6R)-CH$_2$-THF α- + β-cyclodextrin (1:1:1) | — | 80.2 | 57.3 | 50.2 | 47.4 | 44.0 |

CH$_2$-THF = 5,10-methylenetetrahydrofolic acid b) Stability of the sodium salt solutions of (6R)-5,10-methylenetetrahydrofolic acid 60° C./stress test in phosphate buffer

| | Hours | | | | | |
|---|---|---|---|---|---|---|
| | 3 | 6 | 18 | 24 | 30 | 48 |
| without cyclodextrin | 77.7 | 34.4 | 2.8 | — | 0.8 | — |
| α-cyclodextrin | — | 84.1 | — | — | — | 12.6 |
| β-cyclodextrin | 91.2 | — | — | 75.2 | — | — |
| dimethyl-β-cyclodextrin | 88.9 | — | — | 31.5 | — | — |
| hydroxypropyl-β-cyclodextrin | 90.4 | — | — | 70.5 | — | — |
| γ-cyclodextrin | 95.4 | — | — | 63.5 | — | — |
| hydroxypropyl-γ-cyclodextrin | 97.4 | — | — | 73.7 | — | — | c) Stability of the calcium salt solution of (6R)-5,10-methylenetetrahydrofolic acid at 60° C./stress test in phosphate buffer (PBS)

| | Hours | | | | | |
|---|---|---|---|---|---|---|
| | 3 | 6 | 18 | 24 | 30 | 48 |
| without cyclodextrin | 74.4 | 53.8 | — | 7.7 | 2.6 | 0.1 |
| α-cyclodextrin | 74.5 | 56.4 | — | 7.8 | 3.8 | 0.8 |
| hydroxypropyl-α-cyclodextrin (0.6) | 75.3 | 57.1 | — | 7.8 | 2.7 | 0.7 |
| β-cyclodextrin | 87.7 | 77.8 | — | 42.0 | 33.3 | 14.8 |
| dimethyl-β-cyclodextrin (1.8) | 80.2 | 69.1 | — | 29.6 | 22.2 | 7.4 |
| hydroxypropyl-β-cyclodextrin (0.6) | 83.8 | 71.2 | — | 28.8 | 22.5 | 6.2 |
| hydroxypropyl-β-cyclodextrin (0.9) | 83.5 | 69.6 | — | 29.1 | 21.5 | 7.6 |
| γ-cyclodextrin | 81.2 | 66.2 | — | 16.2 | 8.8 | 1.2 |
| hydroxypropyl-γ-cyclodextrin (0.6) | 95.1 | 81.4 | — | 13.6 | 6.8 | 1.0 | d) Stability of the magnesium salt solution of (6R)-5,10-methylenetetrahydrofolic acid at 60° C./stress test in phosphate buffer (PBS)

| | Hours | | | | |
|---|---|---|---|---|---|
| | 3 | 6 | 18 | 24 | 30 |
| without cyclodextrin | 72.7 | 53.4 | — | 7.6 | 2.4 |
| α-cyclodextrin | 76.5 | 58.8 | — | 12.9 | 4.9 |
| hydroxypropyl-α-cyclodextrin (0.6) | 80.2 | 67.4 | — | 14.0 | 6.3 |
| β-cyclodextrin | 79.1 | 61.6 | — | 26.7 | 17.4 |
| dimethyl-β-cyclodextrin (1.8) | 73.6 | 56.3 | — | 19.5 | 11.5 |
| hydroxypropyl-β-cyclodextrin | 83.3 | 64.3 | — | 25.0 | 14.3 |

-continued

|  | Hours | | | | |
| --- | --- | --- | --- | --- | --- |
|  | 3 | 6 | 18 | 24 | 30 |
| (0.6) hydroxypropyl-β-cyclodextrin | 82.6 | 65.1 | — | 24.4 | 12.8 |
| (0.9) γ-cyclodextrin | 82.1 | 64.3 | — | 20.2 | 10.8 |
| hydroxypropyl-γ-cyclodextrin (0.6) | 81.2 | 64.7 | — | 17.6 | 8.9 |

The values given in the tables in each case correspond to the content of 5,10-methylenetetrahydrofolic acid in percent of the starting value (t=0).

For the determination of the stability, solutions were employed having a concentration of about 4% of 5,10-methylenetetrahydrofolic acid at pH 7, prepared according to Examples 3–20. The aim of the experiments was in each case to obtain measurements comparable to those in one of the Tables a, b, c or d. Under optimally selected conditions, which can be determined easily in simple experiments by variation of the concentration of 5,10-methylenetetrahydrofolic acid or cyclodextrin respectively or by variation of their concentration ratio or by the choice of the salt of 5,10-methylenetetrahydrofolic acid or by the choice of the solvent, the stability of the inclusion compound is distinctly higher.

Cyclodextrins having the following water contents were employed for the preparation of the substances in the following examples: α-cyclodextrin 11.5%, β-cyclodextrin 15.6%, dimethyl-β-cyclodextrin 12.7%, hydroxypropyl-β-cyclodextrin 6.4%, γ-cyclodextrin 9.8%, dimethyl-γ-cyclodextrin 9.2%, hydroxypropyl-γ-cyclodextrin 6.0% (all values determined by means of thermogravimetric analysis).

Example 2

Chemical shift of cyclodextrin inclusion compounds of 5,10-methylenetetrahydrofolic acid in comparison to a mixture of cyclodextrin and 5-formyltetrahydrofolic acid The change in the screening (Δppm) of the $^{13}C$ signals of 5,10-methylenetetrahydrofolic acid or the $^{13}C$ signals of 5-formyltetrahydrofolic acid and the $^1H$ signals of 5,10-methylenetetrahydrofolic acid due to the formation of the inclusion compound with β-cyclodextrin was measured at pH 9 in aqueous solutions.

|  |  | Δppm |
| --- | --- | --- |
| $^{13}C$ spectra | | |
| 5,10-methylenetetrahydrofolic acid | C-7 | +0.532 |
|  | C-9 | +0.908 |
|  | C-11 | +1.301 |
| 5-formyltetrahydrofolic acid | C-7 | +0.013 |
|  | C-9 | +0.013 |
|  | C-11 | −0.007 |
| $^1H$ spectra | | |
| 5,10-methylenetetrahydrofolic acid | $H_2$-7 | +0.20 |
|  | H-3'/H-5' | −0.15 |
|  | H-2'/H-6' | +0.07 |
|  | $H_2$-γ-Glu | −0.08 |

From the Δppm values of the $^{13}C$ spectra of 5-formyltetrahydrofolic acid, it is clear that cyclodextrin does not interact with this substance. In contrast to this, the Δppm values of the $^{13}C$ spectra and the $^1H$ spectra of 5,10-methylenetetrahydrofolic acid indicate an extremely strong interaction, especially in the pteridine moiety of the molecule.

Example 3

β-Cyclodextrin inclusion compounds of (6R)-5,10-methylenetetrahydrofolic acid 22.7 g of β-cyclodextrin and 4.88 g of (6S)-tetrahydrofolic acid are suspended in 2000 ml of water under nitrogen at room temperature. 1.3 ml of formalin solution (36.2%) are then added dropwise. By slight warming of the suspension to about 40° C., a virtually clear solution is obtained which, after a clarifying filtration, is concentrated to dryness in a rotary evaporator at 20° C./1 mbar.

25.8 g of β-cyclodextrin inclusion compound of (6R)-5,10-methylenetetrahydrofolic acid are obtained having a content of (6R)-5,10-methylenetetrahydrofolic acid of 13.3% (determined by means of HPLC).

Example 4

β-Cyclodextrin inclusion compound of the sodium salt of (6R)-5,10-methylenetetrahydrofolic acid a) 22.7 g of β-cyclodextrin are suspended in 650 ml of water. 4.8 g of (6S)-tetrahydrofolic acid are added at room temperature under nitogen. In the course of this, the pH of the suspension is kept at 7–9 (16.3 ml of 1N NaOH). 0.93 ml of formalin solution (36.2%) is then added dropwise. The resulting solution is subjected to clarifying filtration and, after an additional reaction time of about 20 minutes, concentrated to dryness at 20° C./1 mbar at room temperature.

26.3 g of β-cyclodextrin inclusion compound of the sodium salt of (6R)-5,10-methylenetetrahydrofolic acid are obtained having a content of (6R)-5,10-methylenetetrahydrofolic acid of 17.9% (determined by means of HPLC).

b) A similar product to that described in Example 4a) is obtained by intensive trituration of 10 g of moist β-cyclodextrin and 2.6 g of (6R)-5,10-methylenetetrahydrofolic acid sodium salt.

Stability of solid: content of (6R)-5,10-methylenetetrahydrofolic acid after 113 days/−25° C. 100.0%, after 63 days/+23° C. 98.2%.

Example 5

β-Cyclodextrin inclusion compound of the calcium salt of (6R)-5,10-methylenetetrahydrofolic acid 5.78 g of β-cyclodextrin and 320 mg of calcium hydroxide are suspended in 30 ml of water. 1.97 g of (6S)-tetrahydrofolic acid are added under nitrogen. 28 ml of water and 0.37 ml of formalin solution (36.2%) are then added. The resulting solution is subjected to clarifying filtration and the inclusion compound is precipitated from the filtrate at 0° C. using 300 ml of ethanol. The product is washed with ethanol/water and dried at 20° C.

7.7 g of β-cyclodextrin inclusion compound of the calcium salt of (6R)-5,10-methylenetetrahydrofolic acid are obtained having a content of (6R)-5,10-methylenetetrahydrofolic acid of 25.6% (determined by means of HPLC).

Example 6

β-Cyclodextrin inclusion compound of the potassium salt of (6R)-5,10-methylenetetrahydrofolic acid The β-cyclodextrin inclusion compound of the potassium salt of (6R)-5,10-methylenetetrahydrofolic acid is prepared in a manner analogous to that described in Example 4.

Example 7

β-Cyclodextrin inclusion compound of the magnesium salt of (6R)-5,10-methylenetetrahydrofolic acid The β-cyclodextrin inclusion compound of the magnesium salt of (6R)-5,10-methylenetetrahydrofolic acid is prepared in a manner analogous to that described in Example 5.

Example 8

α- and β-cyclodextrin inclusion compounds of the calcium salt of (6R)-5,10-methylenetetrahydrofolic acid 10.85 g of α-cyclodextrin, 12.9 g of β-cyclodextrin and 744 mg of calcium hydroxide are suspended in 100 ml of water. 4.93 g of (6S)-tetrahydrofolic acid, a further 31 mg of calcium hydroxide and 0.92 ml of formalin solution (36.2%) are added under nitrogen. After an additional reaction time of about 20 minutes has expired, the solution is subjected to clarifying filtration and the inclusion compound is precipitated from the filtrate at 0° C. by addition of 750 ml of ethanol, washed with ethanol/water and dried at 20° C.

29.2 g of α-/β-cyclodextrin inclusion compound of (6R)-5,10-methylenetetrahydrofolic acid are obtained having a content of (6R)-5,10-methylenetetrahydrofolic acid of 16.5% (determined by means of HPLC).

Example 9

β-Cyclodextrin inclusion compound of the sodium salt of (6S)-5,10-methylenetetrahydrofolic acid 2.27 g of β-cyclodextrin are suspended in 100 ml of water. 608 mg of (6S)-5,10-methylenetetrahydrofolic acid are added under nitrogen at room temperature. In the course of this, the pH of the suspension is kept at 7–9 (2.7 ml of 1N NaOH). The resulting solution is subjected to clarifying filtration and lyophilized.

2.75 g of β-cyclodextrin inclusion compound of the sodium salt of (6S)-5,10-methylenetetrahydrofolic acid are obtained having a content of (6S)-5,10-methylenetetrahydrofolic acid of 16.0% (determined by means of HPLC).

Stability of solid: content of (6S)-5,10-methylenetetrahydrofolic acid-THF after 156 days/–25° C. 100.0%.

Example 10

β-Cyclodextrin inclusion compound of the sodium salt of (6R)-5,10-methylenetetrahydrofolic acid from the sulphate 22.7 g of β-cyclodextrin are suspended in 1130 ml of water. 5.4 g of (6R)-5,10-methylenetetrahydrofolic acid sulphate are added under nitrogen at room temperature. In the course of this, the pH of the suspension is kept at 7–9 (33 ml of 1N NaOH). The resulting solution is subjected to clarifying filtration and lyophilized.

28.4 g of β-cyclodextrin inclusion compound of the sodium salt of (6R)-5,10-methylenetetrahydrofolic acid are obtained having a content of (6R)-5,10-methylenetetrahydrofolic acid of 15.3% (determined by means of HPLC).

Stability of solid: content of sodium salt of (6R)-5,10-methylenetetrahydrofolic acid after 154 days/–25° C. 99.5%.

Example 11

β-Cyclodextrin inclusion compound of (6R)-5,10-methylenetetrahydrofolic acid from a solution 2.27 g of β-cyclodextrin are dissolved in 150 ml of water at 25° C. 608 mg of (6R)-5,10-methylenetetrahydrofolic acid are added under nitrogen (pH 3.7). The resulting solution is subjected to clarifying filtration and the filtrate is lyophilized.

2.7 g of β-cyclodextrin inclusion compound of (6R)-5,10-methylenetetrahydrofolic acid are obtained having a content of (6R)-5,10-methylenetetrahydrofolic acid of 15.5% (determined by means of HPLC).

Stability of solid: content of (6R)-5,10-methylenetetrahydrofolic acid after 158 days/–25° C. 100.0%.

Example 12

β-Cyclodextrin inclusion compound of the sulphate of (6R)-5,10-methylenetetrahydrofolic acid By the use of 540 mg of sulphuric acid salt of (6R)-5,10-methylenetetrahydrofolic acid analogously to Example 11, 2.65 g of β-cyclodextrin inclusion compound of the sulphuric acid salt of (6R)-5,10-methylenetetrahydrofolic acid are obtained having a content (6R)-5,10-methylenetetrahydrofolic acid of 15.2% (determined by means of HPLC).

Stability of solid: content of (6R)-5,10-methylenetetrahydrofolic acid sulphate after 157 days/–25° C. 99.0%.

Example 13

β-Cyclodextrin inclusion compound of the benzenesulphonate of (6R)-5,10-methylenetetrahydrofolic acid By the use of 603 mg of benzenesulphonic acid salt of (6R)-5,10-methylenetetrahydrofolic acid analogously to Example 11, 2.94 g of β-cyclodextrin inclusion compound of the benzenesulphonic acid salt of (6R)-5,10-methylenetetrahydrofolic acid are obtained having a content of (6R)-5,10-methylenetetrahydrofolic acid of 13.1% (determined by means of HPLC).

Stability of solid: content of (6R)-5,10-methylenetetrahydrofolic acid benzenesulphonate after 72 days/–25° C. 100.0%.

Example 14

β-Cyclodextrin inclusion compound of the calcium salt of (6R)-5,10-methylenetetrahydrofolic acid By the use of 610 mg of calcium salt of (6R)-5,10-methylenetetrahydrofolic acid analogously to Example 11, 2.65 g of β-cyclodextrin inclusion compound of the calcium salt of (6R)-5,10-methylenetetrahydrofolic acid are obtained having a content of (6R)-5,10-methylenetetrahydrofolic acid of 15.6% (determined by means of HPLC).

Example 15

β-Cyclodextrin inclusion compound of the magnesium salt of (6R)-5,10-methylenetetrahydrofolic acid By the use of 600 mg of magnesium salt of (6R)-5,10-methylenetetrahydrofolic acid analogously to Example 11, 2.69 g of β-cyclodextrin inclusion compound of the magnesium salt of (6R)-5,10-methylenetetrahydrofolic acid are obtained having a content of (6R)-5,10-methylenetetrahydrofolic acid of 13.1% (determined by means of HPLC).

Stability of solid: content of magnesium salt of (6R)-5,10-methylenetetrahydrofolic acid after 155 days/–25° C. 99.5%.

Example 16

Dimethyl-β-cyclodextrin inclusion compound of the sodium salt of (6R)-5,10-methylenetetrahydrofolic acid 26.2 g of dimethyl-β-cyclodextrin are dissolved in 100 ml of water. 5.6 g of (6R)-5,10-methylenetetrahydrofolic acid sulphate are added under nitrogen at room temperature. In the course of this, the pH of the solution is kept at 7–9 (37 ml of 1N NaOH). The resulting solution is subjected to clarifying filtration and lyophilized.

32.6 g of dimethyl-β-cyclodextrin inclusion compound of the sodium salt of (6R)-5,10-methylenetetrahydrofolic acid are obtained having a content of (6R)-5,10-methylenetetrahydrofolic acid of 14.3% (determined by means of HPLC).

Stability of solid: content of sodium salt of (6R)-5,10-methylenetetrahydrofolic acid after 56 days/−25° C. 100%; after 56 days/+25° C. 97.5%.

Example 17

Dimethyl-β-cyclodextrin inclusion compound of the sulphuric acid salt of (6R)-5,10-methylenetetrahydrofolic acid 2.62 g of dimethyl-β-cyclodextrin are dissolved in 10 ml of water. 560 mg of (6R)-5,10-methylenetetrahydrofolic acid sulphate and then 140 ml of water are added under nitrogen at room temperature. The resulting solution is subjected to clarifying filtration and lyophilized.

3.29 g of dimethyl-β-cyclodextrin inclusion compound of the sulphuric acid salt of (6R)-5,10-methylenetetrahydrofolic acid are obtained having a content of (6R)-5,10-methylenetetrahydrofolic acid of 13.6% (determined by means of HPLC).

Example 18

Hydroxypropyl-β-cyclodextrin inclusion compounds of (6R)- or (6S)-5,10-methylenetetrahydrofolic acid The hydroxypropyl-β-cyclodextrin inclusion compounds of (6R)- or (6S)-5,10-methylenetetrahydrofolic acid and its salts are obtained by the use of hydroxypropyl-β-cyclodextrin analogously to Examples 3–17.

Example 19

Hydroxypropyl-γ-cyclodextrin inclusion compounds of (6R)- or (6S)-5,10-methylenetetrahydrofolic acid The hydroxypropyl-γ-cyclodextrin inclusion compounds of (6R)- or (6S)-5,10-methylenetetrahydrofolic acid and its salts are obtained by the use of hydroxypropyl-γ-cyclodextrin analogously to Examples 3–17.

Example 20

Dimethyl-γ-cyclodextrin inclusion compounds of (6R)- or (6S)-5,10-methylenetetrahydrofolic acid The dimethyl-γ-cyclodextrin inclusion compound of (6R)- or (6S)-5,10-methylenetetrahydrofolic acid and its salts are obtained by the use of dimethyl-γ-cyclodextrin analogously to Examples 3–17.

Example 21

Parenteral form of hydroxypropyl-β-cyclodextrin inclusion compound of (6R)-5,10-methylenetetrahydrofolic acid magnesium salt.

30 mg hydroxypropyl-β-cyclodextrin inclusion compound of (6R)-5,10-methylenetetrahydrofolic acid magnesium salt prepared according to Example 18 are dissolved in 30 ml sterile, deaerated, physiologic normal saline water containing 5% dextrose and 0.1M sodium ascorbate (pH<9.5). After filtration through a 0.45 μm filter, the solution is filled into ampoules or transferred into a dropping bottle.

Example 22

Parenteral form of hydroxypropyl-β-cyclodextrin inclusion compound of (6R)-5,10-methylenetetrahydrofolic acid sodium salt.

A solution of 3000 mg hydroxypropyl-β-cyclodextrin inclusion compound of (6R)-5,10-methylenetetrahydrofolic acid sodium salt prepared according to Example 18 in 30 ml sterile deaerated water is filtered through a 0.45 μm filter solution and filled into ampoules or transferred into a dropping bottle.

Example 23

Oral form of hydroxypropyl-β-cyclodextrin inclusion compound of (6R)-5,10-methylenetetrahydrofolic acid sodium salt.

150 mg hydroxypropyl-β-cyclodextrin inclusion compound of (6R)-5,10-methylenetetrahydrofolic acid sodium salt prepared according to Example 18 is pulverized and mixed with 300 mg calcium hydrogen phosphate $2H_2O$, 60 mg corn starch, 100 mg cellulose powder (microcrystalline), 5 mg highly disperse silicic acid (Aerosil 200) and 5 mg magnesium stearate. The mixture is processed to tablets.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A stable aqueous composition comprising:
   an aqueous medium, a 5,10-methylenetetrahydrofolic acid compound, and a cyclodextrin,
   wherein said compound is (6R)-, (6S)- or (6R, S)-5,10-methylenetetrahydrofolic acid or a salt thereof; and
   said cyclodextrin is α-cyclodextrin, β-cyclodextrin, γ-cyclodextrin, a derivative of α-cyclodextrin, a derivative of β-cyclodextrin, a derivative of γ-cyclodextrin or mixtures thereof.

2. A composition according to claim 1, wherein said composition contains (6R)-5,10-methylenetetrahydrofolic acid or a pharmaceutically tolerable salt thereof and β-cyclodextrin, γ-cyclodextrin or a pharmaceutically tolerable derivative thereof.

3. A composition according to claim 1, wherein said compound is a pharmaceutically tolerable alkali metal or alkaline earth metal salt of 5,10-methylenetetrahydrofolic acid, and said cyclodextrin is a hydroxyalkylated or alkylated β- or γ-cyclodextrin.

4. A composition according to claim 2, wherein said compound is a pharmaceutically tolerable alkali metal or alkaline earth metal salt of 5,10-methylenetetrahydrofolic acid, and said cyclodextrin is a hydroxyalkylated or alkylated β- or γ-cyclodextrin.

5. A composition according to claim 3, wherein said compound is a sodium, magnesium, or calcium salt of 5,10-methylenetetrahydrofolic acid.

6. A composition according to claim 3, wherein said cyclodextrin is hydroxy-propyl-β-, hydroxypropyl-γ-, or dimethyl-β-cyclodextrin.

7. A cyclodextrin inclusion compound of α-, β- or γ-cyclodextrin and (6R)-5,10-methylenetetrahydrofolic acid, (6S)-5,10-methylenetetrahydrofolic acid or a salt thereof.

8. A hydroxyalkylcyclodextrin inclusion compound of hydroxyalkyl-β- or hydroxyalkyl-γ-cyclodextrin and (6R)-5,10-methylenetetrahydrofolic acid, (6S)-5,10-methylenetetrahydrofolic acid or a salt thereof.

9. A compound according to claim 8, wherein said compound is a hydroxypropyl-β- or hydroxypropyl-γ-cyclodextrin inclusion compound of (6R)-5,10-methylenetetrahydrofolic acid, (6S)-5,10-methylenetetrahydrofolic acid or a salt thereof.

10. An alkylcyclodextrin inclusion compound of alkylated-β- or alkylated-γ-cyclodextrin and (6R)-5,10-methylenetetrahydrofolic acid, (6S)-5,10-methylenetetrahydrofolic acid or a salt thereof.

11. A compound according to claim 10, wherein said compound is a dimethyl-β- or dimethyl-γ-cyclodextrin inclusion compound of (6R)-5,10-methylenetetrahydrofolic acid, (6S)-5,10-methylenetetrahydrofolic acid or a salt thereof.

12. A compound according to claim 7, wherein said compound is an inclusion compound of a sodium, magnesium or calcium salt of (6R)-5,10-methylenetetrahydrofolic acid or (6S)-5,10-methylenetetrahydrofolic acid.

13. A compound according to claim 8, wherein said compound is an inclusion compound of a sodium, magnesium or calcium salt of (6R)-5,10-methylenetetrahydrofolic acid or (6S)-5,10-methylenetetrahydrofolic acid.

14. A compound according to claim 10, wherein said compound is an inclusion compound of a sodium, magnesium or calcium salt of (6R)-5,10-methylenetetrahydrofolic acid or (6S)-5,10-methylenetetrahydrofolic acid.

15. A process for stabilization of an aqueous solution of (6R)-, (6S)- or (6R, S)-5,10-methylenetetrahydrofolic acid or a salt thereof, said process comprising adding α-, β- or γ-cyclodextrin or a derivative of α-, β- or γ-cyclodextrin to said aqueous solution.

16. A process for the preparation of a cyclodextrin inclusion compound of (6R)-, (6S)- or (6R, S)-5,10-methylenetetrahydrofolic acid or a salt thereof; said process comprising:

reacting (6S)-, (6R)- or (6R, S)-tetrahydrofolic acid or a salt of the corresponding tetrahydrofolic acid with formaldehyde in the presence of α-, β- or γ-cyclodextrin or a derivative of α-, β- or γ-cyclodextrin, optionally converting said acid into a salt or said salt into another salt, and optionally isolating the resultant cyclodextrin inclusion compound.

* * * * *